(12) United States Patent
Miyano

(10) Patent No.: US 9,560,955 B2
(45) Date of Patent: Feb. 7, 2017

(54) ENDOSCOPE OBJECTIVE LENS AND ENDOSCOPE

(71) Applicant: FUJIFILM Corporation, Tokyo (JP)

(72) Inventor: Hitoshi Miyano, Saitama-ken (JP)

(73) Assignee: FUJIFILM Corporation, Tokyo (JP)

( * ) Notice: Subject to any disclaimer, the term of this patent is extended or adjusted under 35 U.S.C. 154(b) by 418 days.

(21) Appl. No.: 14/151,896

(22) Filed: Jan. 10, 2014

(65) Prior Publication Data
US 2014/0221752 A1    Aug. 7, 2014

(30) Foreign Application Priority Data

Feb. 4, 2013    (JP) .................. 2013-019217

(51) Int. Cl.
| | |
|---|---|
| A61B 1/06 | (2006.01) |
| A61B 1/04 | (2006.01) |
| H04N 5/225 | (2006.01) |
| G02B 21/02 | (2006.01) |
| G02B 17/00 | (2006.01) |
| G02B 9/00 | (2006.01) |
| A61B 1/00 | (2006.01) |
| G02B 23/24 | (2006.01) |

(52) U.S. Cl.
CPC ......... *A61B 1/00163* (2013.01); *G02B 23/243* (2013.01)

(58) Field of Classification Search
CPC ..... G02B 23/243; G02B 9/58; G02B 13/0045; G02B 23/2484; G02B 3/00; G02B 5/04; G02B 9/12; G02B 9/34; G02B 37/005; A61B 1/00096; A61B 1/0676; A61B 1/00163; A61B 1/05
See application file for complete search history.

(56) References Cited

U.S. PATENT DOCUMENTS

| | | | | |
|---|---|---|---|---|
| 4,598,980 A | * | 7/1986 | Doi .................. | G02B 9/58 359/735 |
| 5,619,380 A | * | 4/1997 | Ogasawara .......... | G02B 9/10 359/661 |
| 6,160,669 A | * | 12/2000 | Nagaoka ............. | G02B 3/0087 359/654 |
| 6,519,098 B2 | * | 2/2003 | Nagaoka ............. | G02B 3/0087 348/552 |
| 6,980,375 B2 | * | 12/2005 | Nagaoka ............. | G02B 3/0087 348/552 |
| 6,994,668 B2 | | 2/2006 | Miyano | |
| 7,554,597 B2 | * | 6/2009 | Scherling ........... | G02B 13/0015 348/335 |

(Continued)

FOREIGN PATENT DOCUMENTS

JP     2004-205779     7/2004

*Primary Examiner* — John P Leubecker
*Assistant Examiner* — Arnaldo Torres Diaz
(74) *Attorney, Agent, or Firm* — Young & Thompson

(57) ABSTRACT

In an endoscope objective lens which includes a reflective member that bends an optical path substantially at a right angle inserted between the last lens surface and an image sensor disposed on the image plane, the effective diameter of the last lens surface is made smaller than the size of the image sensor in a direction corresponding to the optical path bending direction and the endoscope objective lens is made so as to satisfy a conditional expression given below.

$h1 < V + 0.4$    (1)

7 Claims, 8 Drawing Sheets

EXAMPLE 10 (IMAGE SIZE Φ 2.0, ENTIRE AREA ACQUISITION)

(56) References Cited

U.S. PATENT DOCUMENTS

| | | | | |
|---|---|---|---|---|
| 8,164,834 B2* | 4/2012 | Miyano | G02B 23/243 | 359/660 |
| 8,243,129 B2* | 8/2012 | Uzawa | A61B 1/00096 | 348/65 |
| 8,422,150 B2* | 4/2013 | Takato | G02B 13/0045 | 359/715 |
| 8,824,061 B2* | 9/2014 | Tomioka | G02B 15/14 | 359/683 |
| 2001/0040211 A1* | 11/2001 | Nagaoka | G02B 3/0087 | 250/214.1 |
| 2003/0174409 A1* | 9/2003 | Nagaoka | G02B 3/0087 | 359/654 |
| 2006/0268424 A1* | 11/2006 | Miyano | G02B 23/243 | 359/661 |
| 2008/0080061 A1* | 4/2008 | Miyano | G02B 23/243 | 359/661 |
| 2009/0086017 A1* | 4/2009 | Miyano | G02B 23/243 | 348/65 |
| 2011/0043931 A1* | 2/2011 | Li | G02B 9/12 | 359/739 |
| 2012/0224268 A1* | 9/2012 | Takato | G02B 13/0045 | 359/648 |
| 2013/0155212 A1* | 6/2013 | Kamo | G02B 23/243 | 348/65 |
| 2013/0235176 A1* | 9/2013 | Miyano | G02B 13/06 | 348/65 |
| 2014/0015999 A1* | 1/2014 | Miyano | G02B 13/06 | 348/222.1 |
| 2014/0218811 A1* | 8/2014 | Yamamoto | G02B 23/243 | 359/749 |
| 2014/0221752 A1* | 8/2014 | Miyano | G02B 23/243 | 600/162 |
| 2014/0240855 A1* | 8/2014 | Yamamoto | G02B 23/243 | 359/781 |
| 2015/0205074 A1* | 7/2015 | Asami | G02B 13/06 | 359/713 |
| 2015/0212299 A1* | 7/2015 | Yamakawa | G02B 13/18 | 359/714 |

* cited by examiner

EXAMPLE 1 (IMAGE SIZE Φ 2.0, ENTIRE AREA ACQUISITION)

EXAMPLE 1 (IMAGE SIZE Φ 2.0, PARTIAL AREA ACQUISITION)

EXAMPLE 2 (IMAGE SIZE Φ 2.0, ENTIRE AREA ACQUISITION)

EXAMPLE 2 (IMAGE SIZE Φ 2.0, PARTIAL AREA ACQUISITION)

EXAMPLE 3 (IMAGE SIZE Φ 2.0, ENTIRE AREA ACQUISITION)

EXAMPLE 3 (IMAGE SIZE Φ 2.0, PARTIAL AREA ACQUISITION)

EXAMPLE 4 (IMAGE SIZE Φ 2.0, ENTIRE AREA ACQUISITION)

EXAMPLE 4 (IMAGE SIZE Φ 2.0, PARTIAL AREA ACQUISITION)

EXAMPLE 5 (IMAGE SIZE Φ 2.0, ENTIRE AREA ACQUISITION)

EXAMPLE 6 (IMAGE SIZE Φ 2.0, PARTIAL AREA ACQUISITION)

EXAMPLE 7 (IMAGE SIZE Φ 2.0, ENTIRE AREA ACQUISITION)

EXAMPLE 8 (IMAGE SIZE Φ 2.0, PARTIAL AREA ACQUISITION)

EXAMPLE 9 (IMAGE SIZE Φ 2.0, PARTIAL AREA ACQUISITION)

EXAMPLE 10 (IMAGE SIZE Φ 2.0, ENTIRE AREA ACQUISITION)

a. VERTICAL PICTURE SIZE = HORIZONTAL PICTURE SIZE b. VERTICAL PICTURE SIZE < HORIZONTAL PICTURE SIZE

ENDOSCOPE OBJECTIVE LENS AND ENDOSCOPE

BACKGROUND OF THE INVENTION

Field of the Invention

The present invention relates to an endoscope objective lens mounted on a distal end portion of an endoscope and an endoscope provided with the endoscope objective lens.

Description of the Related Art

Recently, in the field of endoscopes, the pernasal type has been put into practical use in addition to the peroral type, and the outer diameter of the distal end of the insertion section has been reduced to about 9 mm for the peroral type and to less than 6 nm for the pernasal type in order to reduce the burden on the patient. Along with this, downsizing of the imaging unit mounted inside of the distal end portion has become essential.

Generally, endoscopes include a cylindrical rigid section with a length of about 20 to 30 mm at the distal end portion and the orientation of the rigid tip section in a body cavity is changed by performing a bending operation of a flexible section coupled to the posterior end of the rigid section. An imaging unit formed of an endoscope objective lens and an image sensor is mounted inside of the rigid tip section and an image of an observation region is captured through an objective window formed in the rigid tip section. Each end of a light guide fiber, an air and water feed tube, a forceps tube, and the like is further coupled to the rigid tip section to allow illumination of an observation region, washing and drying of the objective window, treatment of an affected area or sample collection with an appropriate treatment tool through each corresponding opening.

As an objective lens used for such endoscope as described above, the present applicant has already disclosed an endoscope objective lens described in Japanese Unexamined Patent Publication No. 2004-205779. This endoscope objective lens is configured with an importance on a long back focus in order to allow an optical path bending prism and other optical members, such as filters, including a low-pass filter, a infrared light cut filter, and the like, a cover glass, and the like to be inserted between the last lens surface and the image plane, because it may sometimes be advantageous for diameter reduction to laterally arrange the image sensor by bending the optical path of the lens system.

SUMMARY OF THE INVENTION

In order to implement diameter reduction for the endoscope distal end portion by laterally arranging the image sensor and downsizing the imaging unit formed of the endoscope objective lens and the image sensor, it is necessary to appropriately arrange the position where the optical path is bent in the endoscope objective lens, the position of image plane where the image sensor is disposed, the positions of optical members to be provided in front of the image plane, and the like. In Japanese Unexamined Patent Publication No. 2004-205779, however, these points have not been clearly indicated.

The present invention has been developed in view of the circumstances described above, and it is an object of the present invention to provide an endoscope objective lens that allows downsizing of an imaging unit formed of the endoscope objective lens and an image sensor, and an endoscope provided with the endoscope objective lens.

A first endoscope objective lens of the present invention is an endoscope objective lens with a reflective member that bends an optical path substantially at a right angle inserted between the last lens surface and an image sensor disposed on the image plane, wherein:

the effective diameter of the last lens surface is smaller than the size of the image sensor in a direction corresponding to the optical path bending direction; and the endoscope objective lens satisfies a conditional expression given below:

$$h1 < V + 0.4 \quad (1),$$

where:

h1 is the distance from the point where the optical axis of the lens system intersects with the reflection surface of the reflective member to the image plane (unit: mm); and V is the image height on the image plane (unit: mm).

A second endoscope objective lens of the present invention is an endoscope objective lens with a reflective member that bends an optical path substantially at a right angle inserted between the last lens surface and an optical member provided in front of an image sensor disposed on the image plane, wherein:

the effective diameter of the last lens surface is smaller than the size of the image sensor in a direction corresponding to the optical path bending direction; and the endoscope objective lens satisfies a conditional expression given below:

$$h2 < V + 0.4 \quad (2),$$

where:

h2 is the distance from the point where the optical axis of the lens system intersects with the reflection surface of the reflective member to the optical member (unit: mm); and V is the image height on the image plane (unit: mm).

An endoscope of the present invention includes the first or the second endoscope objective lens of the present invention described above.

The endoscope of the present invention which includes the first endoscope objective lens preferably satisfies a conditional expression (3) given below.

$$V < h1 < P/4 \quad (3),$$

where P is the diameter of a distal end portion of the endoscope.

The endoscope of the present invention which includes the second endoscope objective lens preferably satisfies a conditional expression (4) given below.

$$V < h2 < P/4 \quad (4),$$

where P is the diameter of a distal end portion of the endoscope.

The term "the diameter of a distal end portion of the endoscope" as used herein refers to the diameter of the maximum diameter portion of the endoscope insertion section 30 mm up from the tip.

The first endoscope objective lens of the present invention is an endoscope objective lens with a reflective member that bends an optical path substantially at a right angle inserted between the last lens surface and an image sensor disposed on the image plane, in which the effective diameter of the last lens surface is smaller than the size of the image sensor in a direction corresponding to the optical path bending direction and the endoscope objective lens satisfies a conditional expression given below:

$$h1 < V + 0.4 \quad (1)$$

This allows an imaging unit formed of the endoscope objective lens and the image sensor to be downsized.

The second endoscope objective lens of the present invention is an endoscope objective lens with a reflective member that bends an optical path substantially at a right angle inserted between the last lens surface and an optical member provided in front of an image sensor disposed on the image plane, in which the effective diameter of the last lens surface is smaller than the size of the image sensor in a direction corresponding to the optical path bending direction and the endoscope objective lens satisfies a conditional expression given below:

$$h2 < V + 0.4 \quad (2)$$

This allows an imaging unit formed of the endoscope objective lens and the image sensor to be downsized.

The endoscope of the present invention includes the endoscope objective lens of the present invention, so that the diameter of the distal end portion of the endoscope may be reduced.

DESCRIPTION OF THE PREFERRED EMBODIMENTS

Figure 1:
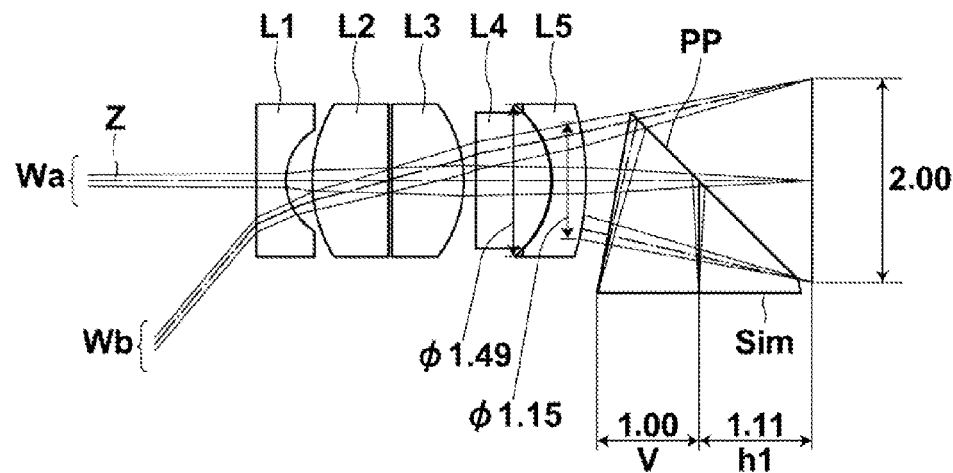
FIG. 1 is a cross-sectional view of an endoscope objective lens according to an embodiment of the present invention (common to Example 1), illustrating a lens configuration thereof (acquisition of the entire image area).
Figure 2:
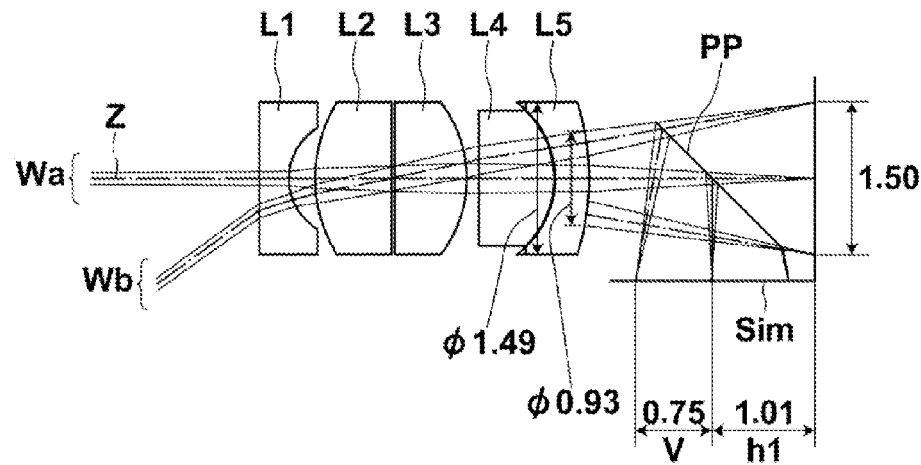
FIG. 2 is a cross-sectional view of the endoscope objective lens described above (acquisition of a part of the image area).

Hereinafter, embodiments of the present invention will be described in detail with reference to the accompanying drawings. FIG. 1 is a cross-sectional view of an endoscope objective lens according to an embodiment of the present invention (common to Example 1), illustrating a lens configuration thereof (acquisition of the entire image area). FIG. 2 is a cross-sectional view of the endoscope objective lens described above (acquisition of a part of the image area). The configuration examples illustrated in FIGS. 1 and 2 are common to that of an endoscope objective lens of Example 1 to be described later. In FIGS. 1 and 2, the left side is the object side and the right side is the image side. Note that FIGS. 1 and 2 illustrate light flux Wb at the maximum angle of view in the bending direction together with axial light flux Wa.

As illustrated in FIGS. 1 and 2, the endoscope objective lens is formed of a negative lens L1, a positive lens L2, a positive lens L3, a positive lens L4, a negative lens L5, and a reflective member PP along the optical axis Z in order from the object side.

Figure 16:
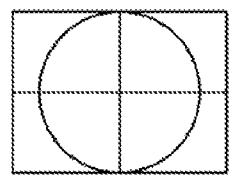
FIG. 16 illustrates arrangement aspect of an image sensor.
Figure 16:
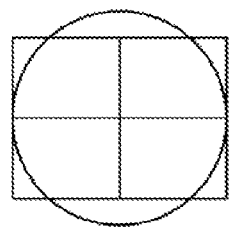
Figure 16:
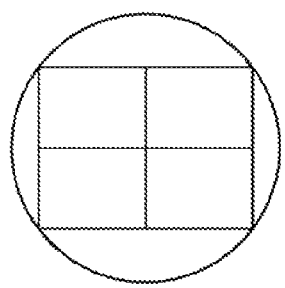

An image sensor, such as a CCD, CMOS, or the like, is disposed on the image plane Sim of the endoscope objective lens. In the present embodiment, it is assumed that an image sensor with an aspect ratio of 4:3 is used, and FIG. 1 illustrates the state in which the image sensor is disposed such that the entire image area of the lens system is obtained (the state indicated by the symbol a in FIG. 16) while FIG. 2 illustrates the state in which the image sensor is disposed such that a part of the image forming area of the lens system is obtained (the state indicated by the symbol b in FIG. 16).

The present endoscope objective lens is configured such that the effective diameter of the last lens surface is smaller than the size of the image sensor in a direction corresponding to the optical path bending direction and so as to satisfy a conditional expression (1) given below, regardless of the arrangement aspect of the image sensor.

$$h1 < V + 0.4 \quad (1)$$

where, h1 is the distance from the point where the optical axis of the lens system intersects with the reflection surface of the reflective member to the image plane (unit: mm) and V is the image height on the image plane (unit: mm).

In an endoscope that uses the endoscope objective lens as described above, the outer diameter of the lens or the distance from the point where the optical axis of the lens system intersects with the reflection surface of the reflective member to the image plane has a large impact on determining the outer diameter of the endoscope distal end portion.

The predominant range of outer diameters of the endoscope objective lenses is 1.0 mm to about 2.0 mm, in which case the lens radius of the last lens surface is about the effective diameter+0.2 mm, and the wall thickness of the lens barrel of the lens portion is also about 0.2 mm.

Thus, the arrangement of the objective lens so as to satisfy the conditional expression (1) described above results in that the position of the image plane lies inside of the outer circumference of the lens barrel in a lens diameter direction. This allows downsizing of the imaging unit formed of the endoscope objective lens and the image sensor.

When applying the endoscope objective lens to an endoscope, optical members, such as filters, including a low-pas filter, an infrared cut filter, a cover glass, and the like, may be disposed in front of the image sensor disposed on the image plane Sim. In such a case, the endoscope objective lens may be configured so as to satisfy a conditional expression (2) given below.

$$h2 < V + 0.4 \quad (2)$$

where h2 is the distance from the point where the optical axis of the lens system intersects with the reflection surface of the reflective member to the optical member (unit: mm) and V is the image height on the image plane (unit: mm).

A specific material which is preferably used for the lens disposed on the most object side in the endoscope objective lens is glass, but transparent ceramics may also be used.

In a case where the present endoscope objective lens is used under harsh environment, it is preferable that a multilayer coating is provided for protection. Further, an antireflective coating for reducing ghost light at the time of use may be provided other than the protection coating.

Still further, various types of filters, such as a low-pass filter, filters that will cut specific wavelength ranges, and the like may be disposed between each lens. Otherwise, a coating having an effect identical to that of one of the filters may be provided on a lens surface of any of the lenses.

Next, numerical examples of the endoscope objective lens of the present invention will be described.

Example 1

Cross-sectional views of an endoscope objective lens of Example 1, which illustrate configurations thereof, are shown in FIG. 1 (acquisition of the entire image area) and FIG. 2 (acquisition of a part of the image area).

Basic lens data and specification data of the endoscope objective lens of Example 1 are shown in Table 1 and Table 2 respectively. Meanings of the symbols in the tables will be described herein below, by taking those of Example 1 as example, but the same applies basically to Examples 2 to 10.

In the lens data in Table 1, The Si column indicates the surface number in which a number i (i=1, 2, 3, - - - ) is given to each surface in a serially increasing manner toward the image side with the most object side surface being taken as the first surface. The Ri column indicates the radius of curvature of the $i^{th}$ surface and the Di column indicates the surface distance between $i^{th}$ surface and $(i+1)^{th}$ surface on the optical axis Z. The Ndj column indicates the refractive index of $j^{th}$ optical element with respect to the d-line (587.6 nm) in which a number j (j=1, 2, 3, - - - ) is given to each optical element in a serially increasing manner toward the image side with the optical element on the most object side being taken as the first optical element, and the vdj column indicates the Abbe number of $j^{th}$ optical element with respect to the d-line.

The sign of the radius of curvature is positive if the surface shape is convex on the object side and negative if it is convex on the image side. Although not shown in the cross-sectional view of the endoscope objective lens, illustrating the configuration thereof, an aperture stop is included in the basic lens data and the word "aperture" is indicated with a surface number in the row of the surface number column corresponding to the aperture stop.

In relation to the exit pupil position, when the distance from the point where the principal ray heading toward the maximum image height in the bending direction intersects with the optical axis to the image forming plane is taken as EP, the F-number of the lens system is taken as F, the effective radius of the last lens surface is taken as e, the maximum image height in the bending direction is taken as V, and the size of the image sensor in the bending direction is taken as 2V, F=EP/2V if e=V because the uppermost ray is parallel to the optical axis and the angle formed between the uppermost ray and the principal ray is equal to the angle formed between the principal ray and the optical axis and F>EP/2V if e<V.

The specification data in Table 2 shows the focal length f', back focus BF', F-number F, size 2V of the image sensor in the bending direction, distance EP from the point where the principal ray heading toward the maximum image height in the bending direction intersects with the optical axis to the image forming plane, and 2V·F.

In the basic lens data and the specification data, degree is used as the unit of angle and mm is used as the unit of length, but other appropriate units may also be used as optical systems are usable even when they are proportionally increased or decreased.

TABLE 1

Example 1 • Lens Data

| Si (Surface Number) | Ri (Radius of Curvature) | Di (Surface Distance) | Ndj (Refractive Index) | vdj (Abbe Number) |
|---|---|---|---|---|
| 1 | ∞ | 0.2905 | 1.88300 | 40.80 |
| 2 | 0.5835 | 0.2573 | | |
| 3 | 1.4185 | 0.7470 | 1.80518 | 25.42 |
| 4 | ∞ | 0.0000 | | |
| 5 (aperture) | ∞ | 0.0332 | | |
| 6 | ∞ | 0.7055 | 1.71300 | 53.90 |
| 7 | −1.2209 | 0.1162 | | |
| 8 | ∞ | 0.7470 | 1.71300 | 53.90 |
| 9 | −0.9337 | 0.3320 | 1.80518 | 25.42 |
| 10 | −2.5174 | | | |

TABLE 2

Example 1 • Specifications (d-line)

| | Vertical Arrangement | Horizontal Arrangement |
|---|---|---|
| f | 1.214 | 1.214 |
| Bf | 2.079 | 2.079 |
| FNo. | 7.061 | 7.061 |
| 2V | 2.00 | 1.50 |
| EP | 4.285 | 4.255 |
| 2V · F | 14.122 | 10.5915 |

Example 2

Figure 3:
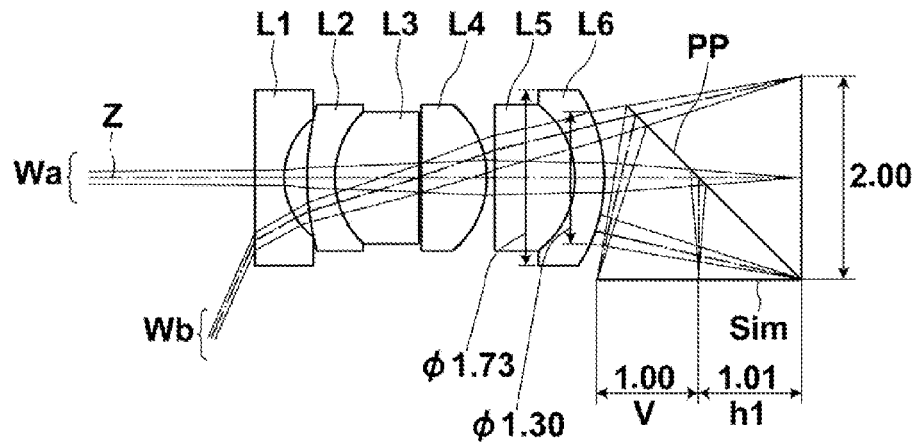
FIG. 3 is a cross-sectional view of an endoscope objective lens of Example 2, illustrating a lens configuration thereof (acquisition of the entire image area).
Figure 4:
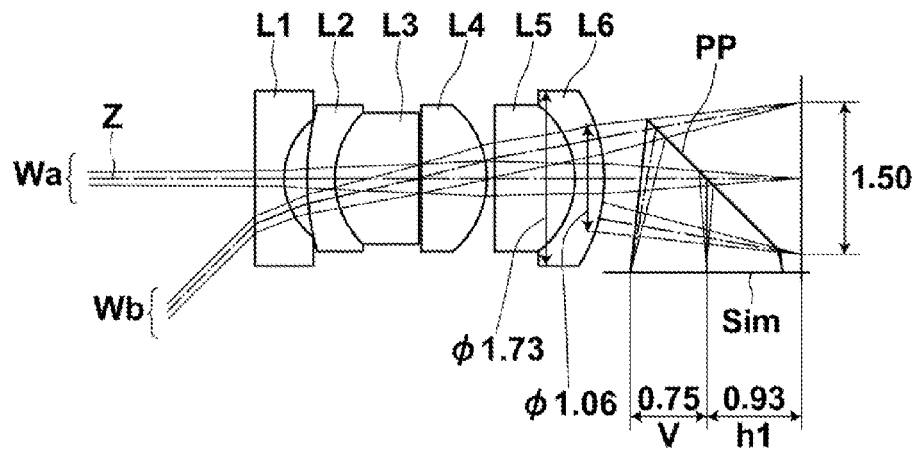
FIG. 4 is a cross-sectional view of the endoscope objective lens of Example 2, illustrating a lens configuration thereof (acquisition of a part of the image area).

Cross-sectional views of an endoscope objective lens of Example 2, which illustrate configurations thereof, are shown in FIG. 3 (acquisition of the entire image area) and FIG. 4 (acquisition of a part of the image area).

Basic lens data and specification data of the endoscope objective lens of Example 2 are shown in Table 3 and Table 4 respectively.

TABLE 3

Example 2 • Lens Data

| Si (Surface Number) | Ri (Radius of Curvature) | Di (Surface Distance) | Ndj (Refractive Index) | νdj (Abbe Number) |
|---|---|---|---|---|
| 1 | ∞ | 0.2880 | 1.88300 | 40.80 |
| 2 | 0.7358 | 0.2256 | | |
| 3 | 2.7655 | 0.2736 | 1.83481 | 42.71 |
| 4 | 0.9000 | 0.8231 | 1.80518 | 25.42 |
| 5 | ∞ | 0.0000 | | |
| 6 (aperture) | ∞ | 0.0252 | | |
| 7 | ∞ | 0.6480 | 1.62041 | 60.30 |
| 8 | −0.9389 | 0.0720 | | |
| 9 | ∞ | 0.7920 | 1.62041 | 60.30 |
| 10 | −0.9000 | 0.2880 | 1.92286 | 18.90 |
| 11 | −1.6097 | | | |

TABLE 4

Example 2 • Specifications (d-line)

| | Vertical Arrangement | Horizontal Arrangement |
|---|---|---|
| f | 0.999 | 0.999 |
| Bf | 1.845 | 1.845 |
| FNo. | 4.507 | 4.507 |
| 2V | 2.00 | 1.50 |
| EP | 4.226 | 4.184 |
| 2V · F | 9.014 | 6.7605 |

Example 3

Figure 5:
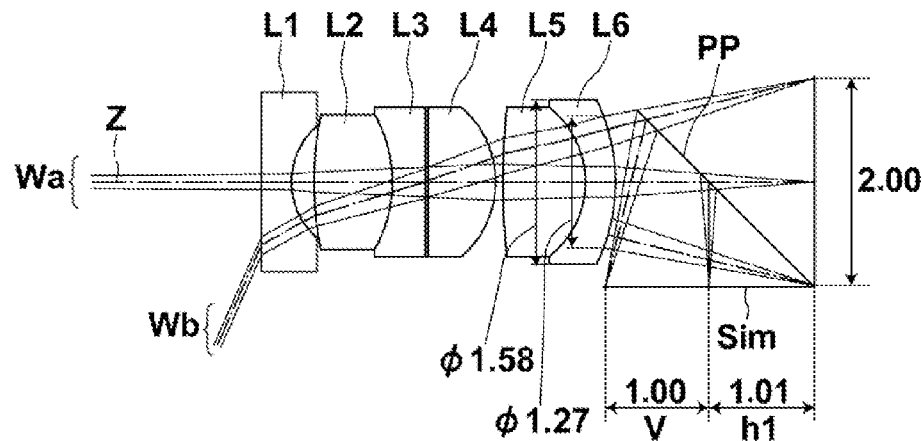
FIG. 5 is a cross-sectional view of an endoscope objective lens of Example 3, illustrating a lens configuration thereof (acquisition of the entire image area).
Figure 6:
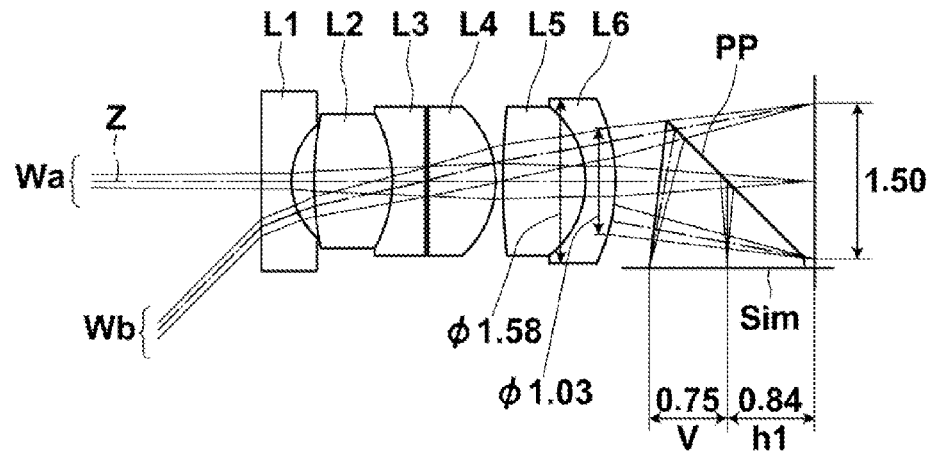
FIG. 6 is a cross-sectional view of the endoscope objective lens of Example 3, illustrating a lens configuration thereof (acquisition of a part of the image area).

Cross-sectional views of an endoscope objective lens of Example 3, which illustrate configurations thereof, are shown in FIG. 5 (acquisition of the entire image area) and FIG. 6 (acquisition of a part of the image area).

Basic lens data and specification data of the endoscope objective lens of Example 3 are shown in Table 5 and Table 6 respectively.

TABLE 5

Example 3 • Lens Data

| Si (Surface Number) | Ri (Radius of Curvature) | Di (Surface Distance) | Ndj (Refractive Index) | νdj (Abbe Number) |
|---|---|---|---|---|
| 1 | ∞ | 0.2880 | 1.88300 | 40.80 |
| 2 | 0.7200 | 0.2160 | | |
| 3 | 3.1155 | 0.7539 | 1.80518 | 25.42 |
| 4 | −1.3113 | 0.3210 | 1.83481 | 42.71 |
| 5 | ∞ | 0.0000 | | |
| 6 (aperture) | ∞ | 0.0252 | | |
| 7 | ∞ | 0.6480 | 1.62041 | 60.30 |
| 8 | −0.9549 | 0.0720 | | |
| 9 | 7.2312 | 0.7920 | 1.62041 | 60.30 |
| 10 | −0.9149 | 0.2880 | 1.92286 | 18.90 |
| 11 | −1.8158 | | | |

TABLE 6

Example 3 • Specifications (d-line)

| | Vertical Arrangement | Horizontal Arrangement |
|---|---|---|
| f | 0.999 | 0.999 |
| Bf | 1.822 | 1.822 |
| FNo. | 6.492 | 6.492 |
| 2V | 2.00 | 1.50 |
| EP | 4.059 | 4.009 |
| 2V•F | 12.984 | 9.738 |

Example 4

Figure 7:
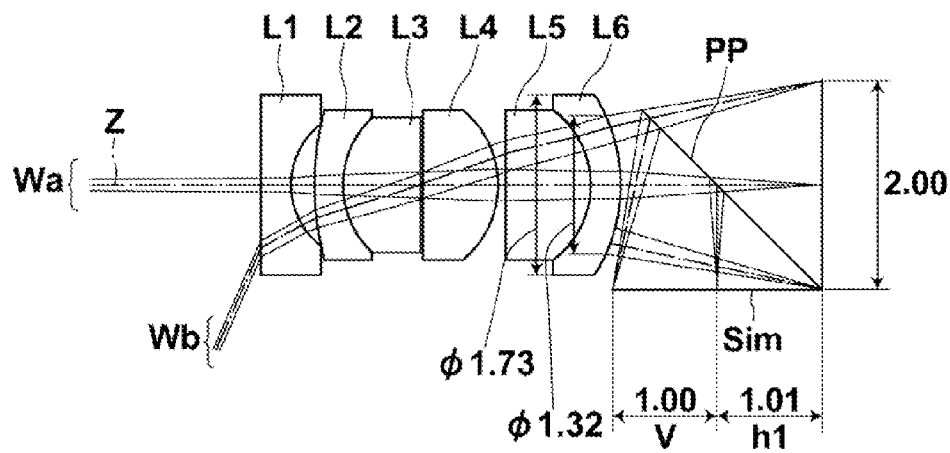
FIG. 7 is a cross-sectional view of an endoscope objective lens of Example 4, illustrating a lens configuration thereof (acquisition of the entire image area).
Figure 8:
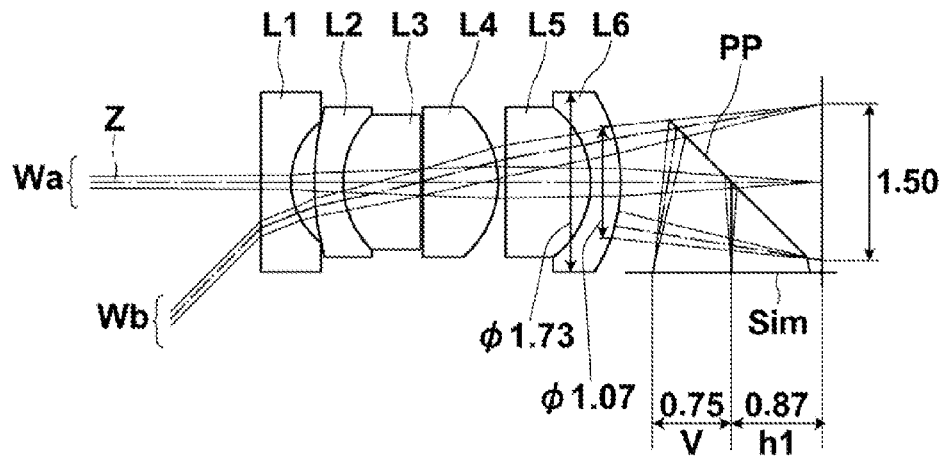
FIG. 8 is a cross-sectional view of the endoscope objective lens of Example 4, illustrating a lens configuration thereof (acquisition of a part of the image area).

Cross-sectional views of an endoscope objective lens of Example 4, which illustrate configurations thereof, are shown in FIG. 7 (acquisition of the entire image area) and FIG. 8 (acquisition of a part of the image area).

Basic lens data and specification data of the endoscope objective lens of Example 4 are shown in Table 7 and Table 8 respectively.

TABLE 7

Example 4 • Lens Data

| Si (Surface Number) | Ri (Radius of Curvature) | Di (Surface Distance) | Ndj (Refractive Index) | ν dj (Abbe Number) |
|---|---|---|---|---|
| 1 | ∞ | 0.2880 | 1.88300 | 40.80 |
| 2 | 0.7358 | 0.2256 | | |
| 3 | 2.7655 | 0.2736 | 1.83481 | 42.71 |
| 4 | 0.9000 | 0.7416 | 1.80518 | 25.42 |
| 5 | ∞ | 0.0000 | | |
| 6 (aperture) | ∞ | 0.0252 | | |
| 7 | ∞ | 0.7200 | 1.62041 | 60.30 |
| 8 | −0.9389 | 0.0720 | | |
| 9 | ∞ | 0.8136 | 1.62041 | 60.30 |
| 10 | −0.9000 | 0.2880 | 1.92286 | 18.90 |
| 11 | −1.6049 | | | |

TABLE 8

Example 4 • Specifications (d-line)

| | Vertical Arrangement | Horizontal Arrangement |
|---|---|---|
| f | 0.998 | 0.998 |
| Bf | 1.836 | 1.836 |
| FNo. | 4.394 | 4.394 |
| 2V | 2.00 | 1.50 |
| EP | 4.531 | 4.482 |
| 2V•F | 8.788 | 6.591 |

Example 5

Figure 9:
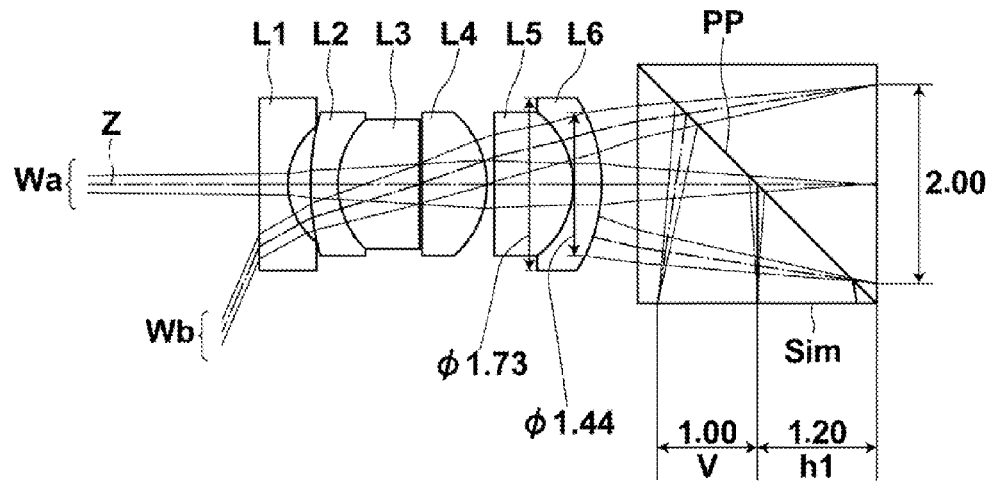
FIG. 9 is a cross-sectional view of an endoscope objective lens of Example 5, illustrating a lens configuration thereof.

A cross-sectional view of an endoscope objective lens of Example 5, which illustrates a configuration thereof, is shown in FIG. 9.

Basic lens data and specification data of the endoscope objective lens of Example 5 are shown in Table 9 and Table 10 respectively.

TABLE 9

Example 5•Lens Date

| Si (Surface Number) | Ri (Radius of Curvature) | Di (Surface Distance) | Ndj (Refractive Index) | ν dj (Abbe Number) |
|---|---|---|---|---|
| 1 | ∞ | 0.2880 | 1.88300 | 40.80 |
| 2 | 0.7358 | 0.2256 | | |
| 3 | 2.7655 | 0 2736 | 1.83481 | 42.71 |
| 4 | 0.9000 | 0.8231 | 1.80518 | 25.42 |
| 5 | ∞ | 0.0000 | | |
| 6(aperture) | ∞ | 0.0252 | | |
| 7 | ∞ | 0.6480 | 1.62041 | 60.30 |
| 8 | −0.9389 | 0.0720 | | |
| 9 | ∞ | 0.7920 | 1.62041 | 60.30 |
| 10 | −0.9000 | 0.2880 | 1.92286 | 18.90 |
| 11 | −1.6097 | 0.3590 | | |
| 12 | ∞ | 2.4000 | 1.51680 | 64.20 |
| 13 | ∞ | | | |

TABLE 10

Example 5•Specifications (d-line)

| | |
|---|---|
| f | 0.999 |
| Bf | 1.845 |
| FNo. | 4.531 |
| 2V | 2.00 |
| EP | 4.482 |
| 2V•F | 9.062 |

Example 6

Figure 10:
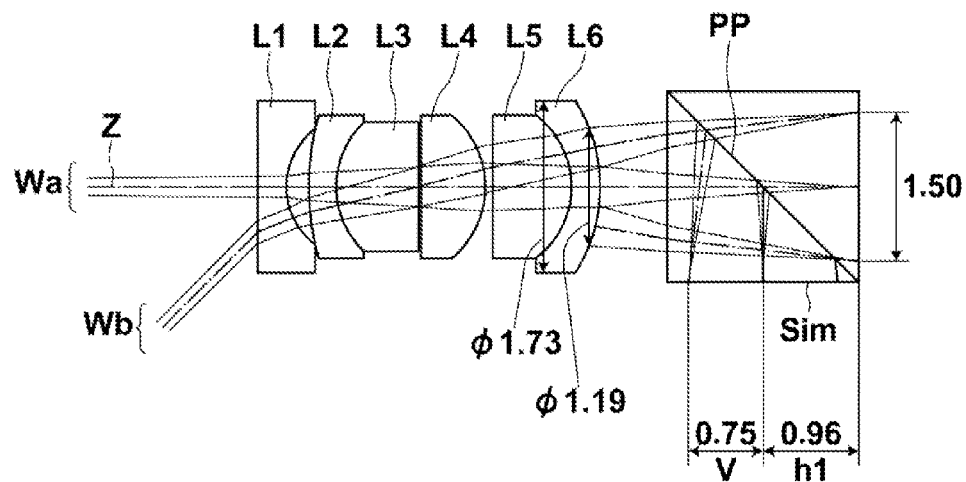
FIG. 10 is a cross-sectional view of an endoscope objective lens of Example 6, illustrating a lens configuration thereof.

A cross-sectional view of an endoscope objective lens of Example 6, which illustrates a configuration thereof, is shown in FIG. 10.

Basic lens data and specification data of the endoscope objective lens of Example 6 are shown in Table 11 and Table 12 respectively.

TABLE 11

Example 6•Lens Data

| Si (Surface Number) | Ri (Radius of Curvature) | Di (Surface Distance) | Ndj (Refractive Index) | ν dj (Abbe Number) |
|---|---|---|---|---|
| 1 | ∞ | 0.2880 | 1.88300 | 40.80 |
| 2 | 0.7358 | 0.2256 | | |
| 3 | 2.7655 | 0.2736 | 1.83481 | 42.71 |
| 4 | 0.9000 | 0.8231 | 1.80518 | 25.42 |
| 5 | ∞ | 0.0000 | | |
| 6(aperture) | ∞ | 0.0252 | | |
| 7 | ∞ | 0.6480 | 1.62041 | 60.30 |
| 8 | −0.9389 | 0.0720 | | |
| 9 | ∞ | 0.7920 | 1.62041 | 60.30 |
| 10 | −0.9000 | 0.2880 | 1.92266 | 18.90 |
| 11 | −1.6097 | 0.6750 | | |
| 12 | ∞ | 1.9200 | 1.51680 | 64.20 |
| 13 | ∞ | | | |

TABLE 12

Example 6•Specifications (d-line)

| | |
|---|---|
| f | 0.999 |
| Bf | 1.845 |
| FNo. | 4.507 |

TABLE 12-continued

Example 6•Specifications (d-line)

| | |
|---|---|
| 2V | 1.50 |
| EP | 4.482 |
| 2V•F | 6.7605 |

Example 7

Figure 11:
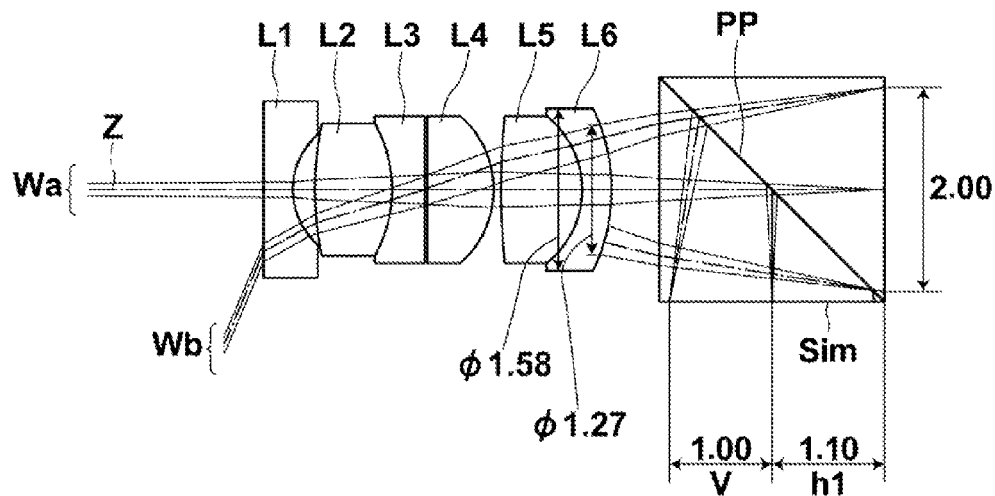
FIG. 11 is a cross-sectional view of an endoscope objective lens of Example 7, illustrating a lens configuration thereof.

A cross-sectional view of an endoscope objective lens of Example 7, which illustrates a configuration thereof, is shown in FIG. 11.

Basic lens data and specification data of the endoscope objective lens of Example 7 are shown in Table 13 and Table 14 respectively.

TABLE 13

Example 7•Lens Data

| Si (Surface Number) | Ri (Radius of Curvature) | Di (Surface Distance) | Ndj (Refractive Index) | ν dj (Abbe Number) |
|---|---|---|---|---|
| 1 | ∞ | 0.2880 | 1.88300 | 40.80 |
| 2 | 0.7200 | 0.2160 | | |
| 3 | 3.1155 | 0.7539 | 1.80518 | 25.42 |
| 4 | −1.3113 | 0.3210 | 1.83481 | 42.71 |
| 5 | ∞ | 0.0000 | | |
| 6 (aperature) | ∞ | 0.0252 | | |
| 7 | ∞ | 0.6480 | 1.62041 | 60.30 |
| 8 | −0.9549 | 0.0720 | | |
| 9 | 7.2312 | 0.7920 | 1.62041 | 60.30 |
| 10 | −0.9149 | 0.2880 | 1.92286 | 18.90 |
| 11 | −1.8158 | 0.4680 | | |
| 12 | ∞ | 2.2000 | 1.51680 | 64.20 |
| 13 | ∞ | | | |

TABLE 14

Example 7•Specifications (d-line)

| | |
|---|---|
| f | 0.999 |
| Bf | 1.822 |
| FNo. | 6.492 |
| 2V | 2.00 |
| EP | 4.036 |
| 2V•F | 12.984 |

Example 8

Figure 12:
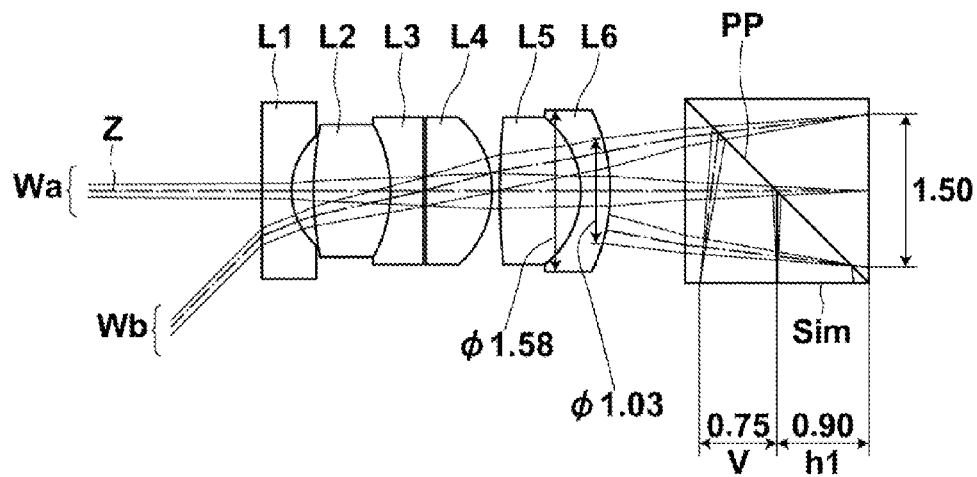
FIG. 12 is a cross-sectional view of an endoscope objective lens of Example 8, illustrating a lens configuration thereof.

A cross-sectional view of an endoscope objective lens of Example 8, which illustrates a configuration thereof, is shown in FIG. 12.

Basic lens data and specification data of the endoscope objective lens of Example 8 are shown in Table 15 and Table 16 respectively.

TABLE 15

Example 8•Lens Data

| Si (Surface Number) | Ri (Radius of Curvature) | Di (Surface Distance) | Ndj (Refractive Index) | ν dj (Abbe Number) |
|---|---|---|---|---|
| 1 | ∞ | 0 2880 | 1.88300 | 40.80 |
| 2 | 0.7200 | 0.2160 | | |
| 3 | 3.1155 | 0.7539 | 1.80518 | 25.42 |
| 4 | −1.3113 | 0.3210 | 1.83481 | 42.71 |
| 5 | ∞ | 0.0000 | | |
| 6 (aperature) | ∞ | 0.0252 | | |

TABLE 15-continued

Example 8•Lens Data

| Si (Surface Number) | Ri (Radius of Curvature) | Di (Surface Distance) | Ndj (Refractive Index) | ν dj (Abbe Number) |
|---|---|---|---|---|
| 7 | ∞ | 0.6480 | 1 62041 | 60.30 |
| 8 | −0.9549 | 0.0720 | | |
| 9 | 7.2312 | 0.7920 | 1.62041 | 60.30 |
| 10 | −0.9149 | 0.2880 | 1.92286 | 18.90 |
| 11 | −1.8158 | 0.7310 | | |
| 12 | ∞ | 1.8000 | 1.51680 | 64.20 |
| 13 | ∞ | | | |

TABLE 16

Example 8•Specifications (d-line)

| | |
|---|---|
| f | 0.999 |
| Bf | 1.822 |
| FNo. | 6.492 |
| 2V | 1.50 |
| EP | 3.998 |
| 2V•F | 9.738 |

Example 9

Figure 13:
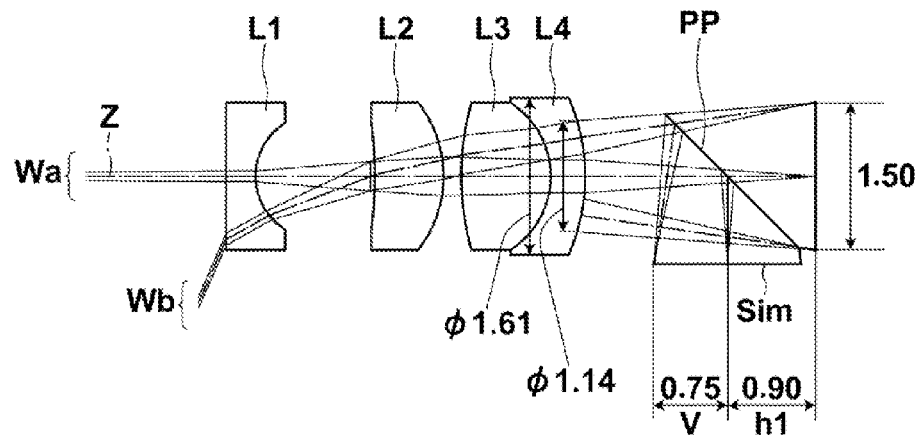
FIG. 13 is a cross-sectional view of an endoscope objective lens of Example 9, illustrating a lens configuration thereof.

A cross-sectional view of an endoscope objective lens of Example 9, which illustrates a configuration thereof, is shown in FIG. 13.

Basic lens data and specification data of the endoscope objective lens of Example 9 are shown in Table 17 and Table 18 respectively.

TABLE 17

Example 9•Lens Data

| Si (Surface Number) | Ri (Radius of Curvature) | Di (Surface Distance) | Ndj (Refractive Index) | ν dj (Abbe Number) |
|---|---|---|---|---|
| 1 | ∞ | 0.4020 | 1.88300 | 40.80 |
| 2 | 0 8630 | 1.5678 | | |
| 3 (aperture) | ∞ | 0.0603 | | |
| 4 | −5.2220 | 0.9380 | 1.71300 | 53.90 |
| 5 | −1.6241 | 0.2412 | | |
| 6 | 3.7306 | 1.2194 | 1.62041 | 60.30 |
| 7 | −1.1953 | 0.4690 | 1.92286 | 18.90 |
| 8 | −2.6733 | | | |

TABLE 18

Example 9•Specifications (d-line)

| | |
|---|---|
| f | 1.051 |
| Bf | 3.044 |
| FNo. | 7.001 |
| 2V | 2.00 |
| EP | 6.632 |
| 2V•F | 14.002 |

Example 10

Figure 14:
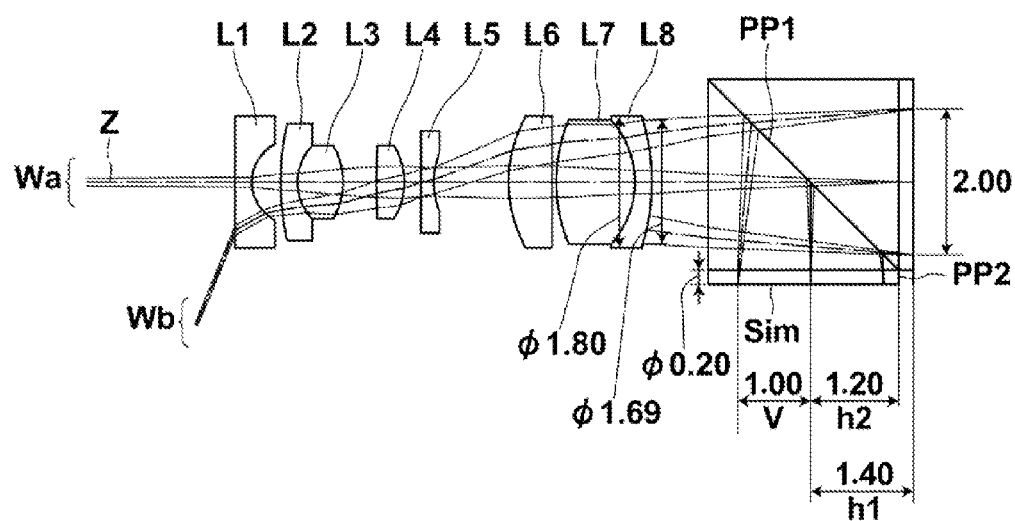
FIG. 14 is a cross-sectional view of an endoscope objective lens of Example 10, illustrating a lens configuration thereof.

A cross-sectional view of an endoscope objective lens of Example 10, which illustrates a configuration thereof, is shown in FIG. 14.

Unlike Examples 1 to 9 described above, present Example includes an optical member PP2, such as a cover glass or the like, between the reflective member PP1 for bending the optical path of the lens system and the image plane Sim.

Basic lens data and specification data of the endoscope objective lens of Example 10 are shown in Table 19 and Table 20 respectively.

TABLE 19

Example 10•Lens Data

| Si (Surface Number) | Ri (Radius of Curvature) | Di (Surface Distance) | Ndj (Refractive Index) | ν dj (Abbe Number) |
|---|---|---|---|---|
| 1 | ∞ | 0.2300 | 1.88300 | 40.80 |
| 2 | 0.5877 | 0.3910 | | |
| 3 | 3.6300 | 0.2300 | 1.88300 | 40.80 |
| 4 | 0.7187 | 0.6210 | 1.48749 | 70.23 |
| 5 | −1.0016 | 0.4543 | | |
| 6 | 8.2018 | 0.3853 | 1.51823 | 58.90 |
| 7 | −0.9551 | 0.2300 | | |
| 8(aperature) | ∞ | 0.0000 | | |
| 9 | ∞ | 0.1725 | 1.60300 | 65.44 |
| 10 | 1.0931 | 1.0178 | | |
| 11 | 1.8348 | 0.5923 | 1.48749 | 70.23 |
| 12 | ∞ | 0.0575 | | |
| 13 | 2.2086 | 1.0753 | 1.43875 | 94.93 |
| 14 | −1.2817 | 0.2300 | 1.84666 | 23.78 |
| 15 | −3.0596 | 0.7700 | | |
| 16 | ∞ | 2.6000 | 1.51680 | 64.20 |
| 17 | ∞ | 0.2000 | 1.51680 | 64.20 |
| 18 | ∞ | | | |

TABLE 20

Example 10•Specifications (d-line)

| | |
|---|---|
| f | 1.111 |
| Bf | 2.496 |
| FNo. | 8.092 |
| 2V | 2.00 |
| EP | 7.782 |
| 2V•F | 16.184 |

It is known from the foregoing data that all of the endoscope objective lenses of Examples 1 to 10 satisfy the conditional expression (1) and are endoscope objective lenses that allow downsizing of the imaging unit formed of the endoscope objective lens and the image sensor.

Figure 15:
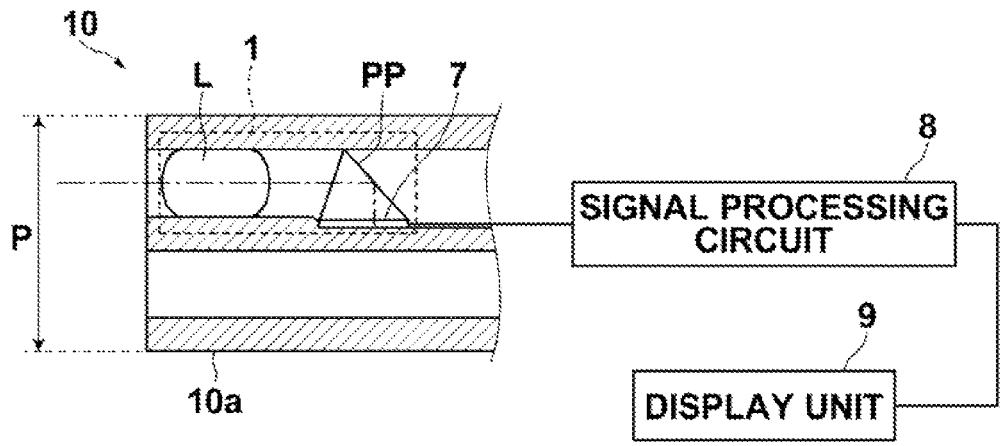
FIG. 15 is a schematic configuration view of an endoscope according to an embodiment of the present invention.

An endoscope according to an embodiment of the present invention will now be described. FIG. 15 is a schematic configuration view of the endoscope according to an embodiment of the present invention. In FIG. 15, each lens is schematically illustrated.

An endoscope 10 illustrated in FIG. 15 includes an imaging unit formed of an endoscope objective lens 1 and an image sensor 7 and disposed near a distal end portion 10a of the insertion section. The image sensor 7 converts an optical image formed by the endoscope objective lens 1 to an electrical signal. As for the image sensor 7, for example, a CCD (Charge Coupled Device), a CMOS (Complementary Metal Oxide Semiconductor), or the like may be used. The image sensor 7 is disposed such that the imaging surface thereof corresponds to the image plane of the endoscope objective lens 1.

The image captured by the endoscope objective lens 1 is formed on the imaging surface of the image sensor 7 and an output signal of the image from the image sensor 7 is subject to arithmetic processing in a signal processing circuit 8 and an image is displayed on a display unit 9.

Here, if the endoscope is configured so as to satisfy a conditional expression (3) given below, the diameter of the endoscope distal end portion may further be reduced.

$$V<h1<P/4 \quad (3)$$

where, V is the image height on the image plane (unit: mm), h1 is the distance from the point where the optical axis of the lens system intersects with the reflection surface of the reflective member to the image plane (unit: mm), and P is the diameter of the endoscope distal end portion.

Optical members, such as filters, including a low-pas filter, an infrared cut filter, a cover glass, and the like may be disposed in front of the image sensor 7 disposed on the image plane. In such a case, the endoscope may be configured so as to satisfy a conditional expression (4) given below.

$$V<h2<P/4 \quad (4)$$

where, V is the image height on the image plane (unit: mm), h2 is the distance from the point where the optical axis of the lens system intersects with the reflection surface of the reflective member to the optical member (unit: mm), and P is the diameter of the endoscope distal end portion.

So far, the present invention has been described by way of embodiments and Examples, but the present invention is not limited to the aforementioned embodiments and Examples and various modifications may be made. For example, values of radius of curvature of each lens, surface distance, refractive index, Abbe number, partial dispersion ratio, aspherical coefficient are not limited to those illustrated in each Example and may take other values.

What is claimed is:

1. An endoscope objective lens, comprising:
   a lens system with an object side and an image side, the lens system including a lens located most toward the image side, wherein a lens surface, of said lens, located closest to the image side of said lens system is a last lens surface of said lens system;
   an image sensor disposed on an image plane; and
   a reflective member that bends an optical path substantially at a right angle located between the last lens surface of the lens system and the image sensor, wherein,
   an effective diameter of the last lens surface is smaller than a size of the image sensor in a direction corresponding an optical path bending direction; and
   the endoscope objective lens satisfies a conditional expression given below:

$$h1<V+0.4 \quad (1)$$

where:
   h1 is a distance in units of mm from a point where an optical axis of the lens system intersects with a reflection surface of the reflective member to the image plane; and
   V is an image height in units of mm on the image plane.

2. An endoscope, comprising the endoscope objective lens of claim 1.

3. The endoscope of claim 2, wherein the endoscope satisfies a conditional expression (3) given below:

$$V<h1<P/4 \quad (3),$$

where P is a diameter in units of mm of a distal end portion of the endoscope.

4. An endoscope objective lens, comprising:
   a lens system with an object side and an image side, the lens system including a lens located most toward the image side, wherein a lens surface, of said lens, located closest to the image side of said lens system is a last lens surface of said lens system;
   an image sensor disposed on an image plane;
   an optical member provided in front of the image sensor; and
   a reflective member that bends an optical path substantially at a right angle located between the last lens surface of the lens system and the optical member, wherein,
   an effective diameter of the last lens surface is smaller than a size of the image sensor in a direction corresponding to an optical path bending direction; and
   the endoscope objective lens satisfies a conditional expression given below:

$$h2<V+0.4 \quad (2),$$

where:
   h2 is a distance in units of mm from a point where an optical axis of the lens system intersects with a reflection surface of the reflective member to the image plane; and
   V is an image height in units of mm on the image plane.

5. An endoscope, comprising the endoscope objective lens of claim 4.

6. The endoscope of claim 5, wherein the endoscope satisfies a conditional expression (4) given below:

$$V<h2<P/4 \quad (4),$$

where P is a diameter in units of mm of a distal end portion of the endoscope.

7. An endoscope, comprising:
   an endoscope objective lens, comprised of
   a lens system with an object side and an image side, the lens system including a lens located most toward the image side, wherein a lens surface, of said lens, located closest to the image side of said lens system is a last lens surface of said lens system;
   an image sensor disposed on an image plane; and
   a reflective member that bends an optical path substantially at a right angle located between the last lens surface of the lens system and the image sensor, wherein,
   the endoscope objective lens satisfies the conditional expressions given below:

$$h1<V+0.4 \quad (1), \text{ and}$$

$$V<h1<P/4 \quad (3)$$

where:
   h1 is a distance in units of mm from a point where an optical axis of the lens system intersects with a reflection surface of the reflective member to the image plane;
   V is an image height in units of mm on the image plane; and
   P is a diameter in units of mm of a leading end of the endoscope.

* * * * *